United States Patent [19]

Hubbard

[11] Patent Number: 5,513,661
[45] Date of Patent: May 7, 1996

[54] USE OF SYMPATHETIC BLOCKADE FOR TREATMENT OF CHRONIC MUSCLE PAIN

[76] Inventor: David R. Hubbard, 4150 Regents Park Row, Ste. 255, La Jolla, Calif. 92037-1467

[21] Appl. No.: 138,453

[22] Filed: Oct. 14, 1993

[51] Int. Cl.⁶ ..................................................... A61B 19/00
[52] U.S. Cl. ............................................................. 128/898
[58] Field of Search ....................................... 128/897–99

[56] References Cited

PUBLICATIONS

Simons, "Muscular Pain Syndromes", (1990) *Adv. Pain Res. Ther.* 17:1–41.
Sola et al., "Incidence of Hypersensitive Areas in Posterior Shoulder Muscles" (1955) *Am. J. Phys. Med.* 34:585–590.
Yunus et al., "Primary Fibromyalgia (Fibrositis): Clinical Study of 50 Patients with Matched Normal Controls" (1981) *Semin. Arthritis Rheum.* 11:151–171.
Bennett, "Beyond Fibromyalgia: Ideas on Etiology and Treatment" (1989) *J. Rheum.* (Suppl. 19) 16:185–191.
Boissevain and McCain, "Toward an Integrated Understanding of Fibromyalgia Syndrome I. Medical and Phathophysiological Aspects" (1991) *Pain* 45:227–238.
Lund et al., "Muscle Tissue Oxygen Pressure in Primary Fibromyalgia" (1986) *Scand. J. Rheum.* 15:165–173.
Simons, "Myofascial Pain Syndromes: Where Are We? Where Are We Going?" (1988) *Arch. Phys. Med. Rehabil.* 69:207–212.
Bengtsson and Henriksson, "The Muscle in Fibromyalgia—A Review of Swedish Studies" (1989) *J. Rheum.* (Suppl. 19) 16:144–149.
Yunus and Kalyan–Raman, "Muscle Biopsy Findings in Primary Fibromyaliga and Other Forms of Nonarticular Rheumatism" (1989) *Rheum. Dis. Clin. North Am.* 15:115–134.
Buchthal and Clemmesen, "On the Differentiation of Palpable Muscle Affections by Electromyography" (1940) *Acta Med. Scand.* 150:48–66.
Elliott, "Tender Muscles in Sciatica" (1944) *Lancet* 1:47–49.
Pozniak–Patewicz, "'Cephalgic' Spasm of Head and Neck Muscles" (1976) *Headache* 4:261–266.
Arroyo, "Electromyography in the Evaluation of Reflex Muscle Spasm" (1966) *J. Florida Med. Assoc.* 53:29–31.
Kraft et al., "The Fibrositis Syndrome" (1968) *Arch. Phys. Med. Rehabil.* 49:155–162.
Durette et al., "Needle Electromygraphic Evaluation of Patients with Myofascial or Fibromyalgic Pain" (1991) *Am. J. Phys. Med. Rehabil.* 70,3:154–156.
McBroom et al., "Electromyography in Primary Fibromyalgia Syndrome" (1988) *Clin. J. Pain* 4:117–119.
Zidar et al., "Quantitative EMG and Muscle Tension in Painful Muscles in Fibromyalgia" (1990) *Pain* 40:249–254.
Dexter and Simons, "Local Twitch Response in Human Muscle Evoked by Palpation and Needle Penetration of a Trigger Point" (1981) *Arch. Phys. Med. Rehabil.* 62:521–522.
Fricton et al., "Myofascial Pain Syndrome: Electromyographic Changes Associated with Local Twitch Response" (1985) *Arch. Phys. Med. Rehabil.* 66:314–316.
Travell, "Symposium on Mechanism and Management of Pain Syndrome" (1957) *Proc. Rudolf Virchow Med. Soc.* 16:128–136.
Travell and Simons, "Myofascial Pain and Dysfunction", *The Trigger Point Manual* (1983) New York, Williams and Williams pp. 13–17.
Malmgren and Hasselmark, "The Platelet and the Neuron: Two Cells in Focus in Migraine" (1988) *Cephalalgia* 8:7–24.
Wolfe et al., "The American Collette of Rheumatology 1990 Criteria for the Classification of Fibromyalgia" (1990) *Arthritis Rheum.* 33,2:160–172.
Gunn et al., "Dry Needling of Muscle Motor Points for Chronic Low–Back Pain" (1980) *Spine* 5,3:279–291.
Cooper, "Trigger–Point Injection: Its Place in Physical Medicine" (1961) *Arch. Phys. Med.* 43:704–709.
Brav and Sigmond, "The Local and Regional Injection Treatment of Low Back Pain and Sciatica" (1941) *Ann. Intern. Med.* 15:840–852.
Frost et al., "A Control, Double–Blind Comparison of Mepivacaine Injection Versus Saline Injection for Myofascial Pain" (1980) *Lancet* 1,3:499–501.
Hendriksson et al., "Muscle Biopsy Findings of Possible Diagnostic Importance in Primary Fibromyalgai . . . " (1982) *Lancet* 2:1395.
Gunn, "Prespondylosis and Some Pain Syndromes Following Denervation Supersensitivity" (1980) *Spine* 5,2:185–192.
Sola and Bonica, Chap 21, *The Management of Pain*, vol. I, 2nd Ed. Lea & Febiger (1990) pp. 354–356.
Ochoa, "Guest Editorial: Essence, Investigation, and Management of Neuropathi Pains . . . " (1993) *Muscle & Nerve* 16,10:997–1008.
Garvey et al., "A Prospective, Randomized, Double–Blind Evaluation of Trigger–Point Injection Therapy for Low-–Back Pain" (1989) *Spine* 14,9:962–964.
Hong, "Myofascial Trigger Point Injection" (1993) *Critical Reviews in Phys. and Rehab.* 0,0:1–15.
Hameroff, "Comparison of Bupivacaine, Etidocaine, and Saline for Trigger–Point Therapy" (1981) *Anesth. Analg.* 60:752–755.
Frost, "Diclofenac Versus Lidocaine as Injection Therapy in Myofascial Pain" (1986) *Scand. J. Rheum.* 15:153–156.
Fine et al., "The Effects of Myofascial Trigger Point Injection are Naloxone Reversible" (1988) *Pain* 32:15–20.

(List continued on next page.)

*Primary Examiner*—William E. Kamm
*Assistant Examiner*—J. P. Lacyk
*Attorney, Agent, or Firm*—Barbara Rae-Venter

[57] ABSTRACT

Methods are provided for intramuscular needle diagnosis and treatment of muscle pain that is believed to be the result of sympathetically mediated spindle spasm. Two simultaneous needle EMG needle recordings are used to establish the presence of and magnitude of the "trigger points" in painful muscle. The abnormal muscle activity so identified can then be treated by blocking the sympathetic activation muscle blocker or other agent that would have the same effect of inhibiting the abnormal muscle activity.

10 Claims, 3 Drawing Sheets

OTHER PUBLICATIONS

Lewit, "The Needle Effect in the Relief of Myofascial Pain" (1979) *Pain* 6:83–90.

Bengtsson et al., "Primary Fibromyalgia, A Clinical Study of 55 Patients" (1986) *Scand. J. Rheum.* 15:340–347.

Bengtsson and Bengtsson, "Regional Sympathetic Blockage in Primary Fibromyalgia" (1988) *Pain* 33:161–167.

Backman et al. "Skeletal Muscle Function in Primary Fibromyalgia" (1988) *Acta Neurol. Scand.* 77:187–191.

Henriksson and Bengtsson, "Muscular Changes in Fibromyalgia and Their Significance in Diagnosis" (1990) *Adv. Pain Res. Therapy* 17:259–267.

Hendler et al., "Myofascial Syndrome: Response to Trigger–Point Injections" (1983) *Psychosomatics* 24, 11:990–999.

Solar, "Trigger Point Therapy" (1985) *Clnical Procedures in Emergency Medicine*, ed. by Roberts and Hedges, Philadephia, W. B. Saunders, pp. 674–686.

Bengtsson et al., "Reduced High–Energy Phosphate Levels in the Painful Muscles of Patients with Primary Fibromyalgia" (1986) *J. Am. Rheum. Assoc.* 29,7:817–821.

USE OF SYMPATHETIC BLOCKADE FOR TREATMENT OF CHRONIC MUSCLE PAIN

INTRODUCTION

1. Technical Field

This invention relates to methods for treating chronic muscle pain using sympathetic blocking agents. The method is exemplified by injection of phenoxybenzamine directly into myofascial trigger points.

2. Background of the Invention

Myofascial pain syndrome is a neuromuscular dysfunction of skeletal muscle fibers manifested by trigger point (TrP) phenomena of various origins and referred phenomena. The underlying pathophysiology of TrPs is unknown. However, specific criteria have been defined for identifying TrPs (Simons, D., (1990) Adv. Pain Res. Ther. 17:1–41; Travell et al. Myofascial pain and dysfunction, the trigger point manual, New York; Williams & Wilkins (1983) 5–44). These criteria include a palpable firm area of muscle, referred to as the taut band; within the taut band, a localized spot of exquisite tenderness to manual pressure, the TrP; a characteristic pattern of pain, tingling, or numbness in response to sustained pressure on the TrP within the taut band; and a local twitch of the taut band when the TrP is distorted transversely. Although the taut band may be several centimeters long, the TrP itself is reported to be only a few millimeters in diameter. The referral phenomena include referred pain, referred tenderness, or referred autonomic phenomena, such as vasoconstriction, coldness, sweating, pilomotor response, ptosis and hypersecretion.

There are both active TrPs that cause clinical pain syndromes, and latent TrPs, which are painless, and not associated with clinical pain syndromes. Latent TrPs are, like active ones, identified by manual palpation of taut bands, tenderness, and characteristic referral pattern of pain in response to sustained manual pressure. Fifty percent of asymptomatic persons have latent TrPs on examination of the shoulder-girdle musculature. Sola et al. (1955) Am. J. Phys. Med. 34:585–90. TrPs can also be distinguished from Tender points (TePs). Tender points are areas of tenderness that may or may not be in muscle tissue, do not have palpable taut bands, and do not refer pain to adjacent areas. Travell et al. Myofascial pain and dysfunction, the trigger point manual, New York; Williams & Wilkins (1983) 5–44).

Patients with a variety of chronic muscle pain syndromes, including tension headaches, neck and lower back problems, fibromyalgia and myofascial pain syndromes present with TrPs in their muscles. It therefore is of interest to determine whether there is spontaneous electromyography (EMG) activity in TrPs, and the cause of this EMG activity as a means for devising treatment regimens for chronic muscle pain.

RELEVANT LITERATURE

Muscle biopsy studies of TrPs have searched for areas of tissue damage (Yunas, et al. (1981) Semin Arthritis Rheum 11:151–71, local hypoxia, Bengtsson, et al. (1986) Arthritis Rheum 29(7):817–21; Bennett, R. M. (1989) J. Rheum (Suppl. 19) 16:185–91; Boessevain, M., McCain, G. (1991) Pain 45:227–38; Lund, et al. (1986) Scand. J. Rheum. 15:165–73; Simons, D. G. (1988) Arch Phys. Med. Rehabil. 69:207–12), or sympathetic hyperactivity, (Bengtsson, A., Henriksson, K. (1989) J. Rheum (Suppl. 19) 16:144–9) but have not shown consistent abnormalities by light microscopy, histochemistry, or electron microscopy (Yunus, M., Kalyan-Raman UP (1989) Rheum Dis. Clin. North Am. 15:115–34).

Needle electromyography (EMG) of painful muscle syndromes has produced variable results. The first was published by Buchtal and Clemmesen in 1940, (Buchtal, F., Clemmesen, S. (1940) Acta. Med. Scand. 150:48–66), who concluded that the spontaneous EMG activity they identified arose in proprioceptive receptors. Since then a number of studies have reported on patients with lumbar disc disease (Elliott, F. A. (1944) Lancet 1:47–9), tension headache (Pozniak-Patewicz E. (1976) Headache 4:261–6), fibrositis (Arroyo, P. (1966) J. Florida Med. Assoc. 53:29–31; Kraft et al. (1968) Arch Phys. Med. Rehabil. 49,I:155–62), fibromyalgia (Durette, et al. (1991) Am. J. Phys. Med. Rehabil. 70,3:154–6; McBroom, et al. (1988) Clin. J. Pain 4:117–9; Zidar, et al. (1990) Pain 40:249–54), and myofascial taut bands (Dexter, J. R., Simons, D. S. (1981) Arch. Phys. Med. Rehabil. 62:521–2; Fricton, et al. (1985) Arch. Phys. Med. Rehabil. 66:314–16). In 1957, Travell described high-frequency firing from TrPs (Travell, J. (1957) Proc. Rudolf Virchow Med. Soc. 16:128–36), BUT IN THE 1983 TrP Manual Travell and Simons concluded that TrPs showed no resting activity and that any activity seen was either insertional or motor unit activity (Travell, J., Simons, D. (1983) Williams & Wilkins 5–44).

SUMMARY OF THE INVENTION

Novel methods for identifying, screening for treatment candidates and treating chronic muscle pain characterized by the presence of myofascial trigger points are provided. The method includes identifying trigger points in muscle by their spontaneous EMG activity then blocking this activity using compositions comprising alpha adrenergic receptor blocking agents. The compositions may be injected intramuscularly into one or more myofascial trigger points, particularly myofascial trigger points in the trapezius. Reversible antagonists may be used to screen treatment candidates; both reversible and irreversible antagonists can be used as a treatment modality. The treatment regimen can be used to inhibit or block the pain and other referral phenomena that result from the spontaneous electromyography activity in trigger points.

DESCRIPTION OF THE PREFERRED EMBODIMENTS

Figure 1:
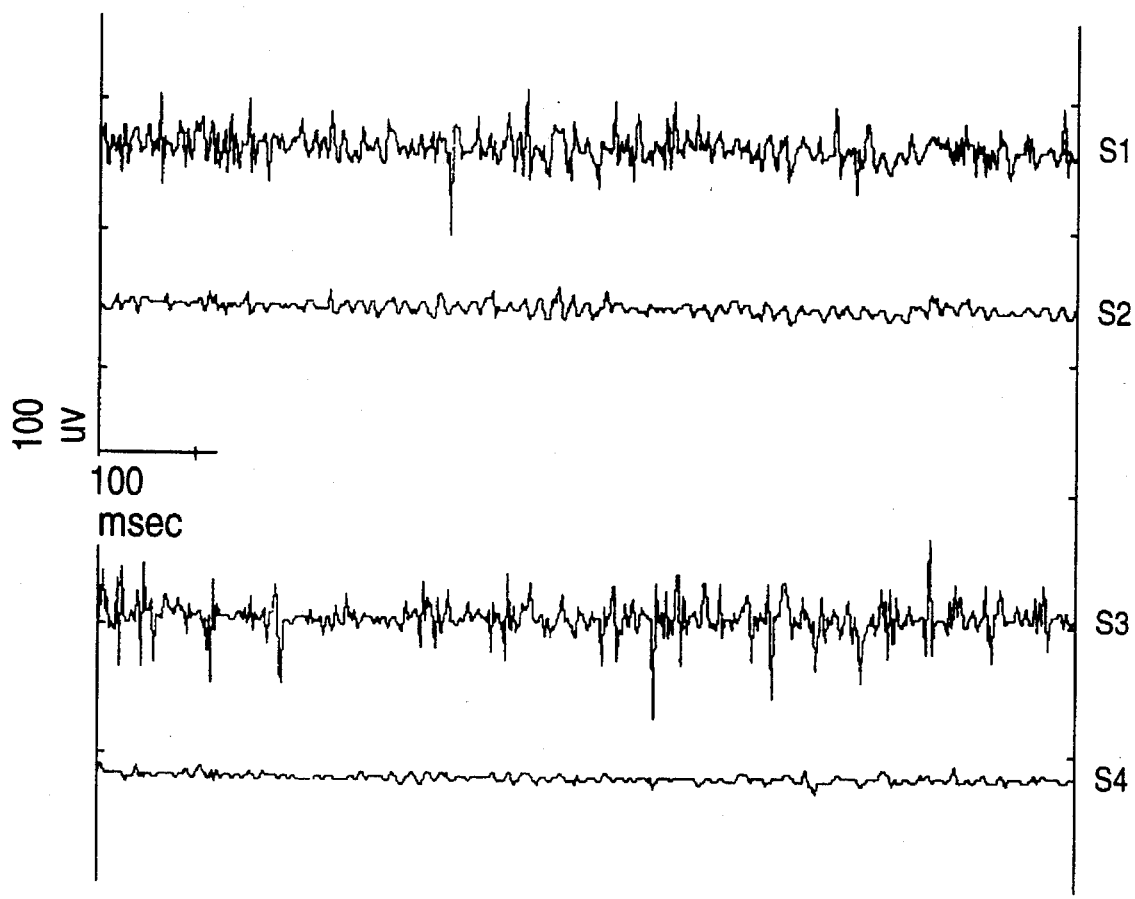
FIG. 1. Spontaneous EMG activity recorded in trapezius trigger point (S1 and S3) and an adjacent nontender site 1 cm away in the same muscle (S2 and S4), in two normal subjects.

In accordance with the subject invention, methods are provided for identifying areas of muscle which are the source of chronic muscle pain and inhibiting or blocking chronic muscle pain in patients identified as potential treatment candidates. The compositions used in the screening and treatment methodologies comprise one or more sympathetic blocking agents which are capable of binding to alpha adrenergic receptors. The agents may be reversible alpha receptor antagonists such as phentolamine or irreversible alpha receptor antagonists such as phenoxybenzamine, preferably irreversible alpha receptor antagonists.

This invention offers several advantages over currently available methods for treating chronic muscle pain. The method of identifying spontaneous EMG activity in TrPs provides information as to which patients are most likely to benefit from treatment with alpha adrenergic blocking agents. The demonstration of sympathetic activity in these myofascial TrPs which is correlatable with the symptoms of the patient, such as referred pain to the ipsilateral cervical, occipital and/or temporal area, can be used as a means of (1) screening patients for those most likely to benefit from therapy and (2) identifying the TrPs which are associated with a clinical pain syndrome. Additionally, the identification of spontaneous sympathetic activity allows use of agents which can specifically treat the pharmacological basis of the pain, on a long term basis, thereby eliminating the need for repeated treatments, such as repeated day needling of the site, or injection of agents such as lidocaine and procaine.

The method includes the steps identifying myofascial trigger points by manual palpation using as criteria palpable firmness of the muscle, tenderness to palpation, typical referral pattern of pain, and when present, a local twitch response (Travell, J., Simons, D.: Myofascial Pain and Dysfunction, the Trigger Manual. New York, Williams and Wilkens, 1983. pp. 13–17), examining identified TrPs by needle EMG, and if spontaneous spike activity is present, injecting the alpha adrenergic antagonist or antagonists directly into the TrP. The screening and treatment methods involve injecting one or more TrP which exhibit spontaneous EMG activity and observing reduction or elimination of the spontaneous activity. Spontaneous activity is defined as electrical activity recorded from muscle or nerve at rest after insertional activity has subsided and when there is no voluntary contraction or external stimulus.

It is important to locate precisely the appropriate TrP and to confirm that they are active TrP associated with a chronic pain syndrome. TrPs are identified in patients with chronic pain by finger palpation for localized (1–3 cm diameter) muscle firmness ("taut band"), tenderness to steady pressure with the thumb or first two fingers and referral of pain in characteristic patterns as described by Simon and Travell, supra. Patients are asked to rate their level of pain during testing as well as prior to testing.

The level of EMG activity in the muscle is then determined by comparing EMG activity in the TrPs with the EMG activity in non-tender fibers (control) of the same muscle. The control EMG activity should be electrically silent and elicit no pain. Generally monopolar disposable needles are used to reduce the risk of infection. Additionally, monopolar needles record from a wider area than concentric bipolar needles which is helpful in demonstrating that areas adjacent to the trigger points are electrically quiet.

The TrP activity can be pinpointed by moving the EMG needle in small (about 1 mm) increments until the patient reports experiencing the same pain and referral pattern as was experienced during manual palpation to identify the TrP. The EMG needle can be withdrawn and inserted until the precise location of the TrP is identified. Once the TrPs are identified precisely, they are then injected with an alpha adrenergic antagonist in an amount sufficient to block the spontaneous EMG activity in the TrPs and thereby inhibit or block the pain associated with the EMG activity in the TrPs.

Where there are several TrPs that meet the criteria indicated above, it may be necessary to inject each TrP before an acceptable level of pain control is reached.

Any of a variety of alpha adrenergic antagonists can be used. Temporary relief can be obtained using transient alpha adrenergic antagonists such as phentolamine. Such agents can also be used as a means of confirming the potential efficacy of using irreversible agents such as phenoxybenzamine or guanethidine as a means for treating a particular patient. Where no relief is obtained using phentolamine, the etiology of chronic pain in such a patient may be due to causes other than simply the EMG activity measured in the TrP and accordingly unlikely to respond to treatment.

The preferred agent for treatment of chronic muscle pain in phenoxybenzamine hydrochloride ("Dibenzyline," SmithKline Beecham Pharmaceuticals). Dibenzyline has a labelled indication only for use in patients with pheochromocytoma to control episodes of hypertension and sweating. It has not previously been used for treatment of chronic muscle pain. The Dibenzyline should be prepared according to the manufacturer's instructions, however, it is given intramuscularly rather than intravenously. There may be some local muscle irritation at the site of intramuscular injection.

Also of interest is guanethidine ("Ismelin," CIBA-GEIGY). The Ismelin should be prepared according to the manufacturer's instructions but given intramuscularly rather than intravenously.

The alpha adrenergic antagonists can be used either alone or in combination with other antagonists.

The subject methods and compositions final use in the treatment of chronic pain associated with myofascial trigger points, including fibromyalgia, myofascial pain syndrome, tension headache and the like. The methods and compositions also can be used as a means of screening for patients who can benefit from treatment, particularly by evaluating the efficacy of reversible antagonists such as phentolamine in blocking spontaneous EMG activity in TrPs.

The following examples are offered by way of illustration and not by way of limitation.

EXAMPLES

Patients presenting to the Neurologic Centre for Headache and Pain with TrPs on physical examination and who agreed to undergo needle EMG were studied. Procedures followed were in accord with the standards for human experimentation. Informed consent was obtained after the nature of the procedure had been fully explained to each subject.

Example 1

Demonstration of Spontaneous Needle EMG Activity in Myofascial Trigger Points

Twenty-nine patients had chronic tension-type headache with pericranial muscle tenderness, diagnosed by a board-certified neurologist according to the criteria of the International Headache Society (International Headache Society, Headache Classification Committee: Classification and diagnostic criteria for headache disorders, *Cephalalgia* (1988) 8:7. These patients had mild to moderate daily fluctuating bilateral frontal and occipital pain and had normal neurologic examinations except for the presence of TrPs. Twenty-five patients met the American College of Rheumatology criteria for fibromyalgia. (Wolfe, F. et al.

(1990) *Arthritis Rheum* 33,2:160–72). These patients had mild to moderate daily fluctuating bilateral neck or shoulder and low-back or buttock pain and had normal neurologic examinations except for the presence of TrPs. No patients had myopathies, neuropathies, radiculopathies, or other significant medical disorders.

We also examined eight normal subjects without history of significant head, neck, or back pain but with latent TrPs on palpatory examination. Normals with latent TrPs were chosen so that needle placement in a TrP could be compared with needle placement in non-TrP muscle fibers. For all subjects and patients, ages ranged from 18 to 80, mean 38.6, mode 36. Eighty percent were women.

Trigger points were identified by finger palpation for localized (1–3 cm diameter) muscle firmness ("taut band"), tenderness to steady pressure with the thumb or first two fingers, and referral of pain in characteristic patterns as described by Simon and Travell (Travell, supra). Trigger points in the upper trapezius were chosen for needle EMG examination because these could be identified in all patients, regardless of site of pain, and in all normal subjects (latent TrPs).

Tenderness rating is as follows: 0, no tenderness; 1, mild tenderness without grimace or flinch; 2, moderate tenderness plus grimace or flinch; 3, severe tenderness plus marked flinch or withdrawal; 4, unbearable tenderness, patient withdraws with light touch. Patients were also asked to rate their level of paid before testing, according to the following scale; 0, no pain; 1, ignorable pain; 2, moderate pain; 3, pain that interferes with one's activity; 4, incapacitating pain requiring bed rest or cessation of activity.

Monopolar TECA disposable EMG needles were inserted through the skin directly over the TrPs. A second needle was placed 1 cm away in nontender fibers of the same muscle. Both needles were referenced to the same equidistant surface electrode. High and low cuts were 10,000 and 30 $H_2$, gain was 100 µV per division, sweep speed was 100 milliseconds per division, displayed ob a 2-channel Cadwell Quantum 84 machine, Kennewick, Washington. After ascertaining that the second site was electrically silent and elicited no pain (hereafter called the non-TrP), the TrP needle was advanced in 1-mm increments until the subject reported experiencing the same pain and referral pattern experienced during manual palpation—the TrP. Typically, this occurred at a depth of about 2 cm, with the patient or subject reporting a deep steady ache or squeezing sensation that radiated to the ipsilateral cervical, occipital or temporal areas as described by Travell and Simons. (Travell, supra) If necessary, the needle was withdrawn and redirected until the precise point could be identified. The needles were left in place for 15–50 minutes.

All EMGs were saved on disc and printed. The Cadwell Quantum 84 Area software was used to calculate the absolute (both negative and positive deflections from the baseline) area-under-the-curve and the mean amplitude for each 1-second interval (the full screen width at a sweep of 100 msec).

No fibrillation potentials or positive sharp waves were seen in any normal subjects or patients. Brief insertional activity could be seen when the needle was first inserted or the subject moved, in which cases both the TrP and the non-TrP needles recorded typical motor unit potentials, which either disappeared spontaneously or could be readily eliminated by relaxing the muscle.

Spontaneous EMG activity was recorded from the TrPs of all normal subjects and patients. The EMG activity disappeared when the TrP needle was moved by as little as 1 mm. No spontaneous activity was recorded from non-TrPs. In all normal subjects and patients, the appearance of the spontaneous EMG activity corresponded to the report of pain, which was described as a deep aching or squeezing sensation, typically associated with a referral of pain upward into the cervical, occipital, or temporal areas, and often associated with autonomic symptoms such as light-headedness, diaphoresis, or nausea. The spontaneous activity was present for as long as the needle was not moved, up to 50 minutes.

Figure 2:
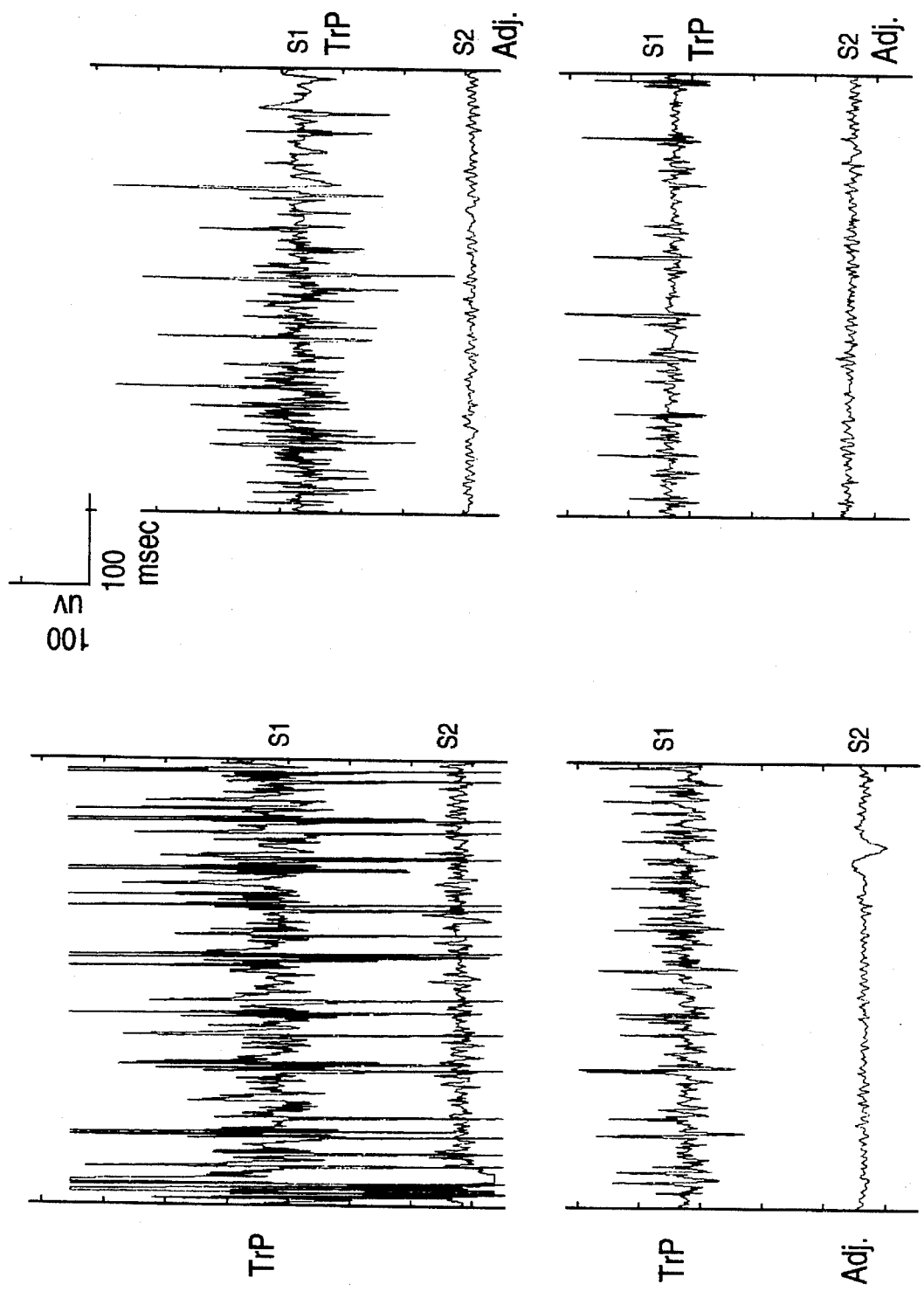
FIG. 2: Spontaneous EMG activity recorded in trapezius trigger point (S1) and an adjacent nontender site 1 cm away in the same muscle (S2), in four patients.

Examples of the spontaneous EMG activity are presented in FIGS. 1 and 2.

Figure 3:
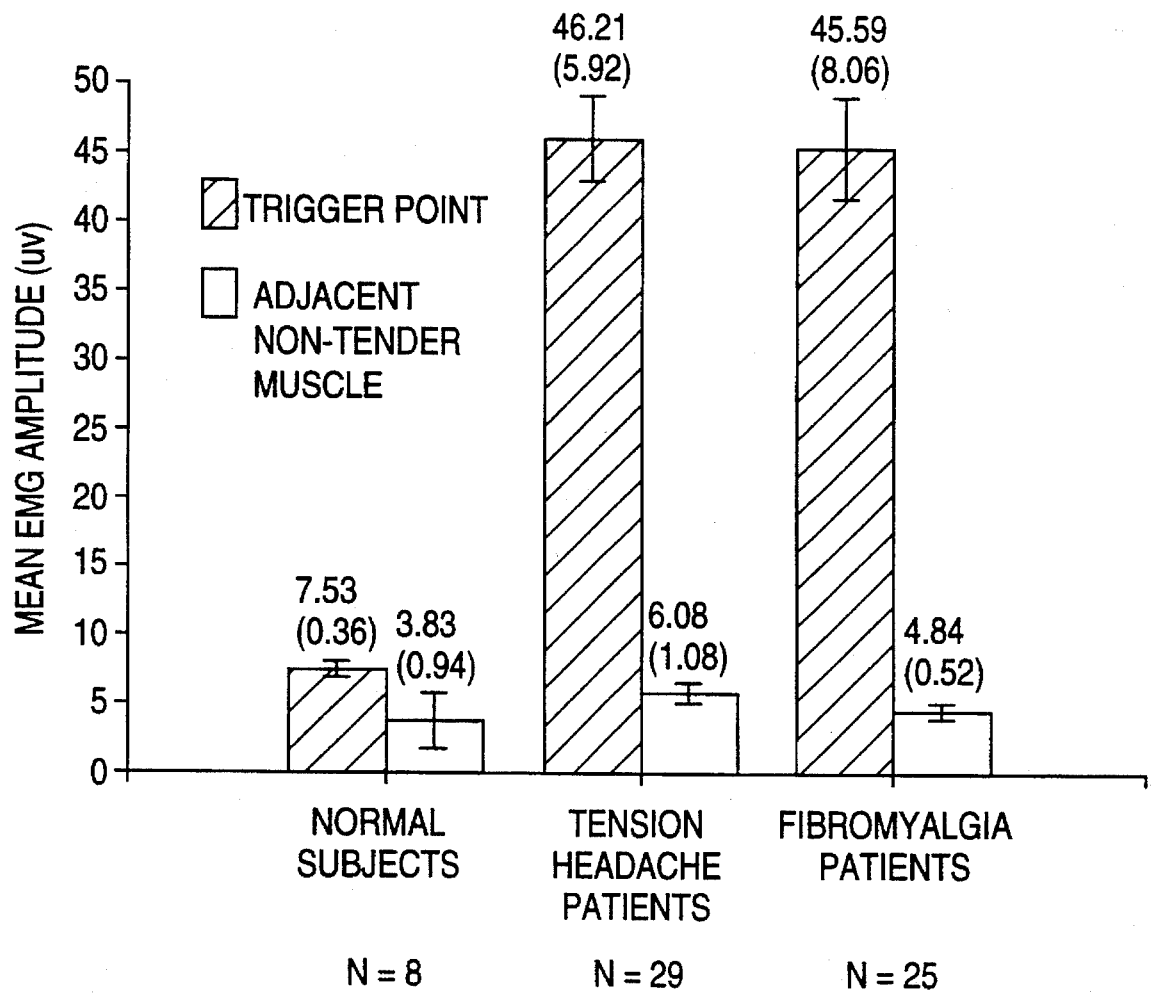
FIG. 3: Mean EMG amplitudes and standard errors ( ) for TrPs and adjacent non-TrPs in trapezius.

FIG. 3 shows the means and standard errors for mean EMG amplitudes for the TrPs and adjacent non-TrPs in normal subjects (latent TrPs) and patient groups (active TrPs). Because unequal sample sizes can exacerbate violations of statistical assumptions, both parametric and nonparametric analyses were run. With either method of analysis, the TrP mean EMG amplitudes for normals were significantly lower than for the two clinical groups, which were not significantly different from each other. In fact, the distributions were nonoverlapping. No normal subject had a mean amplitude greater than 10 uv, and no patient had less than 10 uv.

Pearson correlations between mean EMG amplitude and age, self-reported pain, and tenderness to palpation, and Point Biserial correlations between mean EMG amplitude and sex, were calculated. Correlations were as follows: age: $r(62)=0.07$, not significant (NS); sex: $r(62)=0.12$, NS; pain:$r(59)=0.14$, NS; tenderness: $r(58)=0.43$, $P=0.0007$.

Spontaneous EMG activity was found in the 1–2-mm nidus of myofascial trigger points (TrPs). The activity disappeared if the recording needle was advanced or withdrawn as little as 1 mm. When the needle reached the TrP, the patients consistently reported the onset or aggravation of pain and the characteristic referral pattern of pain. This activity was sustained for as long as we recorded, up to 50 minutes. The second monopolar needle 1 cm distant showed no spontaneous activity, further indicating that the TrP activity was limited to the small area and that no motor unit activity was occurring in adjacent muscle fibers. The TrP EMG mean amplitudes were significantly greater in the two groups of muscle pain patients than in normals. There was no significant difference between the muscle tension headache patients and the fibromyalgia patients. Mean EMG amplitude was significantly correlated with tenderness to palpation of the TrP, but not with self-reported pain, age, or gender.

Example 2

Myofascial Trigger Point Needle EMG Activity Is Increased By A Mental Stressor

Monopolar EMG needles were placed in TrPs and non-TrPs identified as described in Example 1.

Monopolar needle EMG was simultaneously recorded from trapezius TrPs and non-TrPs in 14 normal male and female subjects ages 20–44 during the following conditions: baseline (B1), forward counting (FC), recovery baseline (B2), mental arithmetic stressor (MS), and recovery baseline (B3). The results are shown in the Table below.

TABLE

| | Mean EMG Amplitudes (mean/s,d in microvolts) | | | | |
| --- | --- | --- | --- | --- | --- |
| | B1 | FC | B2 | MS | B3 |
| TrP | 16.8/18.1 | 15.8/10.1 | 15.7/14.6 | 28.3/20.8 | 15.9/12.5 |
| Non-TP | 4.5/3.6 | 4.3/2.0 | 4.6/4.0 | 4.4/2.3 | 4.3/2.0 |

TrP EMG was significantly greater than non-TP in all conditions. The stress condition showed a significant increase in TrP EMG activity over all non-stress conditions, but showed no change in non TP EMG. Thus, a mental stressor increased TrP EMG activity without increased motor unit activity in adjacent muscle fiber areas. These results are consistent with the theory that TrP EMG activity arises in intrafusal muscle fibers which are sympathetically activated.

Example 3

Treatment of Chronic Myofascial Pain with Phentolamine

Fifty patients with myofascial trigger point pain syndromes were evaluated and the location of their TrPs determined as described in Example 1. The effects of phentolamine (5–10 mg) iv or injected directly into a TrP was compared to intramuscular injection of lidocaine or bubivicaine directly into a TrP during recording. Phentolamine, lidocaine and bubivicaine all eliminated the TrP EMG activity within 2–20 minutes.

Example 4

Treatment of Chronic Myofascial Pain With Phenoxybenzamine and Guanethidine

A study similar to that described in Example 3 is carried out to evaluate the efficacy of treatment of myofascial trigger points associated with fibromyalgia with the two sympathetic blockers, guanethidine and phenoxybenzamine. It is hypothesized that local sympathetic blockade of myofascial trigger points will produce long-lasting reduction of pain and tenderness to palpation.

Patients presenting to the Neurologic Centre for Headache and Pain with a clinical diagnosis of fibromyalgia are invited to participate.

Inclusionary criteria:

1. diagnosis of fibromyalgia according to the American College of Rheumatology criteria.
2. males and females between 20 and 60.
3. no other clinically significant medical or psychiatric problems.
4. informed consent Exclusionary criteria:

1. hypotension
2. concomitant use of sympathetic or mimetic medications such as propranolol.

All patients are evaluated by a board-certified neurologist.

Myofascial trigger points are identified by manual palpation according to the criteria of Simons and Travel:

palpable firmness within the muscle
tenderness to palpation
typical referral pattern of pain
local twitch response (not required for inclusion)

Identified TrPs will then be examined by needle EMG. If spontaneous spike activity as described in Example 1 is identified then phenoxybenzamine, 5 mg is injected directly into the TrP.

Blood pressure and heart rate are monitored for 30 minutes. The patient is asked to keep a daily pain log and return at weekly intervals for one month, then at monthly intervals for 4 months.

Self-support of pain, and tenderness and firmness to palpation, and medication use, and functional disability (time at bed rest, time lost from work) are assessed at weekly intervals for one month, then at monthly intervals for 4 months. Post-injection scores for each interval are compared to pre-injection.

This invention thus provides a mechanism of pathogenesis for chronic pain; the sympathetic activity provides a mechanism by which local injury and nociception causes local tension, and by which emotional factors cause widespread tension and pain.

An objective method of diagnosis and evaluation of chronic pain and improved treatment regimen are also provided.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method for reducing chronic pain, said method comprising:

locating at least one myofascial trigger point in a muscle; and contacting the myofascial trigger point with a sufficient amount of an alpha adrenergic antagonist to inhibit spontaneous EMG spike activity in said myofascial trigger point, whereby said chronic pain is reduced.

2. The method according to claim 1, wherein said locating step is performed in a trapezium muscle.

3. The method according to claim 1, wherein said alpha adrenergic antagonist is selected from the group consisting of phentolamine, phenoxybenzamine and guanethidine.

4. A method for identifying a source of chronic pain, said method comprising:

locating at least one muscle causing said chronic pain; and identifying spontaneous EMG spike activity in a myofascial trigger point in said muscle, whereby said trigger point is said source of chronic pain.

5. A method for identifying patients with chronic pain susceptible to treatment with alpha adrenergic antagonists, said method comprising:

locating at least one myofascial trigger point, having spontaneous EMG activity, within a muscle causing said chronic pain; and contacting said myofascial trigger point with an alpha adrenergic antagonist, whereby said patients with chronic pain susceptible to treatment are identified by a reduction in said spontaneous EMG spike activity.

6. The method of claim 1, further comprising the steps of:

contacting said muscle with an EMG detector; and identifying said spontaneous EMG spike activity.

7. The method of claim 1, wherein said contacting step further comprises directly delivering said alpha adrenergic antagonist to the myofascial trigger point.

8. The method of claim 7, wherein said delivering is localized injection.

9. The method of claim 5, wherein said alpha adrenergic antagonist exerts a reversible pharmacologic effect on said myofascial trigger point.

10. The method according to claim 9, wherein said alpha adrenergic antagonist is phentolamine.

* * * * *